United States Patent [19]
Boncella et al.

[11] Patent Number: 5,712,354
[45] Date of Patent: Jan. 27, 1998

[54] BRIDGED METALLOCENE COMPOUNDS

[75] Inventors: James M. Boncella; David E. Richardson; Faisal A. Shafiq, all of Gainesville, Fla.

[73] Assignee: Mobil Oil Corporation, Fairfax, Va.

[21] Appl. No.: 677,800

[22] Filed: Jul. 10, 1996

[51] Int. Cl.$^6$ .................. C08F 4/44; C07F 17/00; C07F 7/00

[52] U.S. Cl. .................. 526/127; 556/11; 556/12; 556/28; 556/27; 556/53; 556/7; 556/87; 556/402; 556/465; 502/153; 502/154; 502/158; 526/132; 526/160; 526/943; 526/352

[58] Field of Search .................. 556/11, 12, 28, 556/27, 53, 7, 402, 465; 526/160, 176, 943, 352, 127, 132; 502/153, 154, 158

[56] References Cited

FOREIGN PATENT DOCUMENTS 2165927 6/1996 Canada.
0716092 7/1995 European Pat. Off..

OTHER PUBLICATIONS

J. Chem. Soc., Chem. Commun., 1995, "Anionic and Zwitterionic Metallocene Complexes Derived From Novel Boratocyclopentadienyl Ligands", pp. 2081–2082.

*Primary Examiner*—Porfirio Nazario-Gonzalez
*Attorney, Agent, or Firm*—Marina V. Schneller; Dennis P. Santini

[57] ABSTRACT

The invention relates to new transition metal compounds useful as olefin polymerization catalysts. They are characterized by the formula (V)(E)(W)M(L), which in which M is a transition metal, V, E, and W, is e.g. alkyl, and L is a ligand which has the formula:

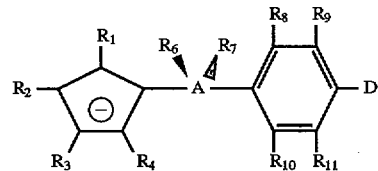

19 Claims, No Drawings

BRIDGED METALLOCENE COMPOUNDS

FIELD OF THE INVENTION

The invention relates to new metallocene compounds. In particular, the new compounds are metallocenes of the transition metals selected from the group consisting of hafnium, titanium and zirconium. These compounds can be used as the source of the transition metal in an olefin polymerization catalyst.

SUMMARY OF THE INVENTION

The compounds of the invention comprise those of formula (V) (E) (W) M—L. Preferred compounds within that formula are compounds of formula IA and IB which are defined below,

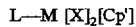  IA.

  IB.

The element L is a ligand defined below in the DETAILED DESCRIPTION OF THE INVENTION, M is a metal selected from the group consisting of zirconium, hafnium and titanium, X is the same or different and is halide (chloride, bromide or iodide) or alkyl, preferably methyl, or aryl; and Y is preferably alkyl. The group Cp' is an unsubstituted or substituted cyclopentadienyl group. Compounds of formula IA can be used in combination with alumoxane to polymerize ethylene. Compounds of IB can be used in the zwitterionic form to polymerize ethylene, without an alumoxane component for activation of the transition metal.

DETAILED DESCRIPTION OF THE INVENTION

The invention relates to transition metal compounds, to their synthesis, and to their use in olefin polymerization, which can be characterized by the formula I', where I' is (V)(E)(W) M—L in which M is selected from the group consisting of zirconium, hafnium and titanium;

each of V, E and W is the same or different and is independently alkyl of 1 to 6 carbon atoms, halide, or unsubstituted or substituted cyclopentadienyl, provided that one, and only one, of said V, E, and W is unsubstituted or substituted cyclopentadienyl; and in which L is

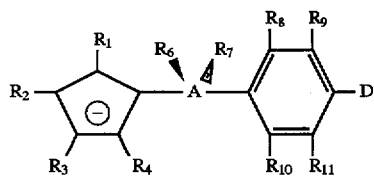

wherein each of $R_1$, $R_2$, $R_3$ and $R_4$ is hydrogen, alkyl of 1 to 6 carbon atoms, alkylene of 2 to 10 carbon atoms which form bridged bicyclic or tricyclic moieties;

A is C, Si, Ge; and each of $R_6$ and $R_7$ is the same or different and is alkyl of 1 to 20 carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$, is the same or different, and is fluorine, hydrogen, alkyl of 1 to 6 carbon atoms;

D is hydrogen, alkyl of 1 to 6 carbon atoms, alkali metal [sodium or lithium]; halogen [chloride or bromide]; alkyl halide in which the alkyl has 1 to 6 carbon atoms and halide is chlorine or bromine; and $BG_3$ or $AlG_3$ in which B is boron (B) or Al is aluminum (Al), and G is pentafluorophenyl, bis-trifluoromethylphenyl, phenyl or alkyl of 1 to 6 carbon atoms.

Preferred compounds of I' are the compounds of formula IA and IB,

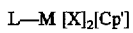  IA.

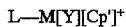  IB.

L refers to a ligand which has the formula

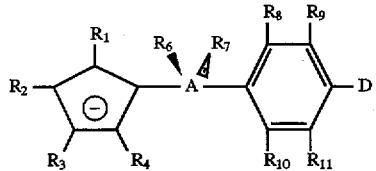

in which each of 1, 2, 3 and 4 is hydrogen, alkyl of 1 to 6 carbon atoms [including methyl, ethyl, propyl, butyl, isobutyl pentyl isomers of pentyl and hexyl and isomers of hexyl], alkylene of 2 to 10 carbon atoms which form bridged bicyclic or tricyclic moieties, (such as indenyl);

A is C, Si, Ge,; and each of $R_6$ and $R_7$ is the same or different and is alkyl of 1 to 20, preferably 1 to 6, carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$, is the same or different, and is fluorine, hydrogen, or alkyl of 1 to 6 carbon atoms;

D is hydrogen, alkyl of 1 to 6 carbon atoms, alkali metal (e.g. sodium or lithium), halogen (chloride or bromide); alkyl halide in which the alkyl has 1 to 6 carbon atoms and halide is chlorine or bromine, and $BG_3$ or $AlG_3$ in which B is boron (B) or aluminum (Al), G is pentafluorophenyl, bis-trifluoromethylphenyl, phenyl or alkyl of 1 to 6 carbon atoms, and M is defined as above.

In the above formula, the Cp' group is an unsubstituted, a mono- or a polysubstituted cyclopentadienyl group. The substituents on the cyclopentadienyl group can be straight-or branched chain $C_1$-$C_6$ alkyl groups. The cyclopentadienyl group can be also a part of a bicyclic or a tricyclic moiety such as indenyl, tetrahydroindenyl, fluorenyl or a partially hydrogenated fluorenyl group, as well as a part of a substituted bicyclic or tricyclic moiety. The cyclopentadienyl groups and L can be also substituted or bridged by polymethylene or dialkylsilane groups, such as —$CH_2$—, —$CH_2$—$CH_2$—, —CR'R"— and —CR'R"—CR'R"— where R' and R" are short alkyl groups or hydrogen, —Si$(CH_3)_2$—, Si$(CH_3)_2$—$CH_2$—$CH_2$—Si$(CH_3)_2$— and similar bridge groups. Suitable groups constituting Cp' include unsubstituted or substituted cyclopentadienyl. Substituted cyclopentadienyls include mono-, di- tri-, tetra- and penta-substituted cyclopentadienyls in which the substituents are alkyl of 1 to 6 carbon atoms [including methyl, ethyl, propyl, butyl, isobutyl, pentyl, isomers of pentyl, hexyl and isomers of hexyl or alkylene groups of 3 to 10 carbon atoms which form bicyclic and tricyclic alicyclic groups. The cyclopentadienyl ring may be mono-, di-, tri-, tetra or penta-substituted. The substitution may be alkyl of 1 to 6 carbon atoms; and thus includes the methylcyclopentadienyl, dimethylcyclopentadienyl, trimethylcylcopentadienyl, tetramethylcyclopentadienyl, pentamethylcyclopentadienyl, ethylcyclopentadienyl, methylethylcyclopentadienyl, propylcyclopentadienyl, methylpropylcyclopentadienyl, butylcyclopentadienyl, methylbutylcyclopentadienyl, and hexylcyclopentadienyl, and an indenyl group, 4,5,6,7-tetrahydroindenyl group and fluorenyl group. These cyclopentadienyl groups may be substituted by a halogen atom or trialkylsilyl group. The lithium compound may comprise said cyclopentadienyl substituted by a second cyclopentadienyl bonded together via an alkylene group such as ethylene and propylene, an isopropylidene group, a substituted alkylene group such as diphenylmethylene, a silylene group or a substituted silylene group such as dimethylsilylene, diphenylsilylene and methylphenylsilylene. The di-, tri, tetra or penta-substituted cyclopentadienyl groups can be dialkyl, trialkyl, tetraalkyl or pentaalkyl-substituted cyclopentadienyl in which the alkyl is 1 to 6 carbon atoms, e.g., methyl, ethyl, propyl, isopropyl, butyl, pentyl, hexyl, and isomers of butyl, pentyl, hexyl.

The ligand L can be synthesized from compounds of formula 1.

The initial synthesis step comprises contacting the compound of formula 1 with a compound of formula a,

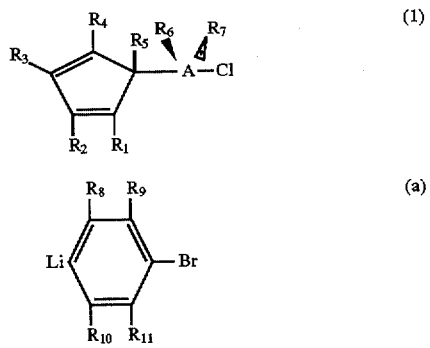

in these compounds of formulae 1 and a, each of $R_1$, $R_2$, $R_3$, $R_4$, $R_5$, $R_6$, $R_7$, $R_8$, $R_9$, $R_{10}$, and $R_{11}$, and A are as defined above; and $R_5$ is preferably hydrogen, although it may be $GeZ_3$ wherein Ge is germanium and Z is alkyl of 1 to 6 carbon atoms [including methyl, ethyl, propyl, butyl, isobutyl, pentyl, hexyl and isomers of pentyl and hexyl and isomers of hexyl] or aryl of 6 to 10 carbon atoms. In preferred embodiments, $R_5$ is hydrogen while each of $R_1$–$R_4$ is methyl; the kinetic inertness of the tetramethylcyclopentadiene proton, when $R_5$ is hydrogen, allows preferential nucleophilic displacement of the A—$C_1$ bond in compound 1 as well as lithiation of component 2 resulting in the high yield synthesis of the compound of formula 4, in subsequent steps. Contact of the two compounds can be undertaken at low temperatures, preferably below ambient temperatures in diethyl ether, for extended periods of time. Compounds of formula I in which $R_1$–$R_4$, $R_6$ and $R_7$ are methyl and A is Si (silicon) are readily available. In preferred embodiments herein the compound of formula a is 1,lithium-4,bromo,-2, 3,5,6-tetrafluorophenyl.

A compound of formula 2 is the product of the contact of the compound of formula 1 and formula a, which is isolatable as a solid compound. The formula of compound(s) 2 is

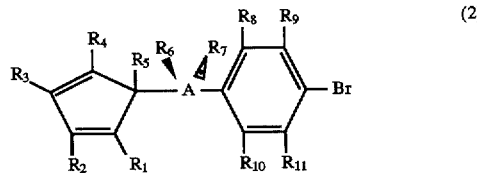

When D is bromine in compound 2, that compound can be further treated with either an alkyl lithium [n-butyllithium] or a Grignard reagent, and subsequently with $B(C_6F_5)_3$ to produce a compound 4, wherein D is —[$B(C_6F_5)_3$] anion. The sequence can be illustrated by the reactions to yield compounds of formulae 3 and 4. Reaction of compound 2 with BuLi will produce a compound of formula 3, which has the structure

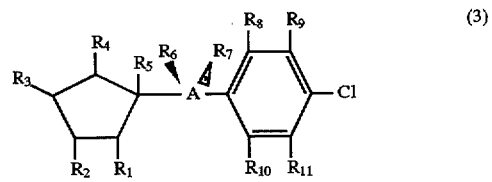

This reaction is undertaken at temperatures below ambient temperature, preferably at −78° C., in diethyl ether. Without isolation, the compound of formula 3 is contacted under substantially the same conditions with $B(C_6F_5)_3$, at −78° C., in diethyl ether for twelve hours to produce the compound of formula 4.

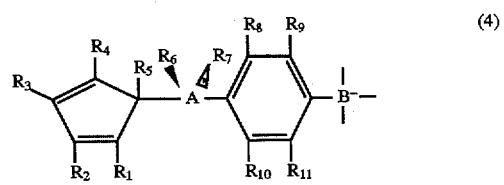

The compound of formula 4 can be converted to a dianion form by abstracting $R_5$ by treatment with alkyl lithium compounds; this step is conducted in diisopropyl ether, which is essential to facilitate the isolation and purification of the compound 4 when it is a dianion, as for example when D is —$BG_3$ in formula 5 and G is $C_6F_5$.

After formation of the of the compound 5, it is contacted with a transition metal chloride, in which the transition metal M is titanium, zirconium or hafnium (III or IV), for example, the tetrahalide or tetrachloride of zirconium, hafnium or titanium. The reaction results in production of a transition metal compound of formula 6

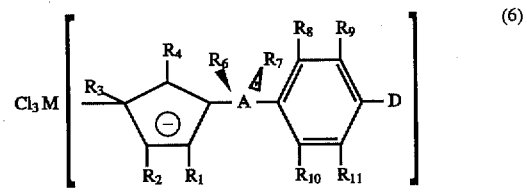

Reaction of the compound of formula 6 with a lithium cyclopentadienyl derivative [in which cyclopentadienyl is denoted by Cp'], in methylene chloride at below ambient temperatures [at −78° C.] results in production of transition metal compound containing two cyclopentadienyl groups which is the compound of formula IA, above.

The cyclopentadienyl moiety in the lithium compound used to convert compound of formula 6, to the compound of formula 1A can be unsubstituted or substituted; if substituted, the cyclopentadienyl ring may be mono-, di-, tri, tetra or penta-substituted. The substitution may be alkyl; and thus includes the methylcyclopentadienyl, dimethylcyclopentadienyl, trimethylcyclopentadienyl, tetramethylcyclopentadienyl, pentamethylcyclopentadienyl, ethylcyclopentadienyl, methylethylcyclopentadienyl, propylcyclopentadienyl, methylpropylcyclopentadienyl, butylcyclopentadienyl, methylbutylcyclopentadienyl, and hexylcyclopentadienyl, and an indenylgroup, 4,5,6,7- tetrahydroindenyl group and fluorenyl group. These cyclopentadienyl groups may be substituted by a halogen atom or trialkylsilyl group. The lithium compound may comprise said cyclopentadienyl substituted by a second cyclopentadienyl bonded together via an alkylene group such as ethylene and propylene, an isopropylidene group, a substituted alkylene group such as diphenylmethylene, a silylene group or a substituted silylene group such as dimethylsilylene, diphenylsilylene and methylphenylsilylene. The di-, tri, tetra or penta-substituted cyclopentadienyl groups can be dialkyl, trialkyl, tetraalkyl or pentaalkyl-substituted cyclopentadienyl in which the alkyl is 1 to 6 carbon atoms, e.g., methyl, ethyl, propyl, isopropyl, butyl, pentyl, hexyl, and isomers of butyl, pentyl, hexyl. Lithium cyclopentadienyl derivatives are readily commercially available.

Reaction of compound of formula IA with a Grignard reagent or an alkyl lithium reagent results in displacement of the halides by alkyl groups to produce compounds of formula IA in which X is alkyl, provided by the Grignard.

Compounds of formula IA can be converted to compounds of formula IB by contacting the alkylated (wherein X is alkyl of 1 to 6 carbon atoms) IA materials with a borane compound including but not limited to $B(C_6F_5)_3$, $Ph_3C^+B(C_6F_5)_4^-$ or $HNR_2Ph^+B(C_6F_5)_4^+$ to abstract an alkyl X group and convert the transition metal compound to a zwitterion for use in polymerization without alumoxane activation. The zwitterion compounds of formula IB may be exemplified by the expression $(V)(E)(L)M+$ or $(V)(W)(L)M+$ or $(E)(W)(L)M+$, in which L includes the group D which is $BG_3$ or $AlG_3$ in which B is boron (B) or aluminum (Al), sodium lithium or halogen and G is selected from the group consisting of pentafluorophenyl, bistrifluoromethylphenyl, hydrogen and alkyl of 1 to 6 carbon atoms. In a catalyst composition the transition metal compounds of IA can be combined with an alumoxane, to activate the compound IA; the amount of alumoxane provides an Al[alumoxane]: transition metal ratio of 50 to 10,000.

Aluminoxanes, e.g. methylalumoxane (MAO), have been used as co-catalyst with metallocene catalysts. The class of alumoxanes (used interchangeably hereinafter with "aluminoxane") comprises oligomeric linear and/or cyclic alkylalumoxanes represented by the formula: $R$—$(Al(R)$—$O)_n$—$AlR_2$ for oligomeric, linear alumoxanes and$(—Al(R)$—$O—)_m$ for oligomeric cyclic alumoxane wherein n is 1–40, preferably 10–20, m is 3–40, preferably 3–20 and R is a $C_1$–$C_8$ alkyl group and preferably methyl. Methylalumoxane is commonly produced by reacting trimethylaluminum with water or with hydrated inorganic salts, such as $CuSO_4 5H_2O$ or $Al_2(SO_4)_3.5H_2O$. Methylalumoxane can be also generated in situ in polymerization reactors by adding trimethylaluminum and water or water-containing inorganic salts. MAO is a mixture of oligomers with a very wide distribution of molecular weights and usually with an average molecular weight of about 1200. MAO is typically kept in solution in toluene.

Conditions for the polymerization and copolymerization of ethylene

The process of the invention may be undertaken in gas phase, in fluid bed gas phase, or in slurry. The catalyst of the invention, allows for the production of linear low density polyethylene in the gas phase or in a slurry polymerization. The products from both the gas phase (e.g. fluid bed) and slurry have a high bulk density, which allows for increased throughput of product per weight of catalyst.

Preferably, the polymerization (copolymerization) is undertaken at a temperature and/or pressure below the sintering temperature of the polymer particles. Most preferably, the process is undertaken in the fluid bed gas phase or in a slurry reactor. The high activity of the catalysts herein allow for efficaceous low pressure fluid bed gas phase and/or slurry process product production. Much lower activity catalysts than those described herein are employed in high pressure processes at pressures which exceed 400 psi, such as solution and high pressure slurry polymerizations. For the production of ethylene copolymers in the process of the present invention an operating temperature of about 30° to 115° C. is preferred, and a temperature of about 70° to 106° C. is most preferred. Temperatures of about 75° to 90° C. are used to prepare products having a density of about 0.91 to 0.92, and temperatures of about 80° to 100° C. are used to prepare products having a density of about 0.92 to 0.94, and temperatures of about 90° to 115° C. are used to prepare products having a density of about 0.94 to 0.96.

In the gas phase, linear low density production is conducted at about 85° C. and high density product is formed at about 105° C. In slurry polymerization, linear low density production is conducted at about 70° C. and high density production is conducted at about 90° C.

In polymerizations described herein, pressures are below 10000 psi, preferably below 1000 psi. The fluid bed reactor is operated at pressures of up to about 1000 psi, and is preferably operated at a pressure of from about 150 to 350 psi, with operation at the higher pressures in such ranges favoring heat transfer since an increase in pressure increases the unit volume heat capacity of the gas.

EXAMPLES

Preparation of $(C_5(CH_3)_4H$—$Si(CH_3)_2$—p—$C_6F_4Br)$ (1): n-BuLi (16.8 mL, 1.6M in hexanes) was carefully injected over a 5 minute period to a –78° C. $Et_2O$ (100 mL) suspension of 1,4-dibromo 2,3,5,6 tetrafluorobenzene ($C_6Br_2F_4$) (12.9 g) and stirred for 10 min. (Caution: n-BuLi addition must be slow and the solution must be kept cold to prevent formation of benzyne and LiF). A $Et_2O$ (15 mL) solution of chlorodimethylsilyl tetramethyl cyclopentadiene $(CH_3)_4(C_5)Si(CH_3)_2$—Cl)H) (8.97 g) was then cannulated over a 7–8 minute period into the flask containing $LiC_6F_4Br$. A yellow solution formed immediately. The solution was left stirring at –78° C. for 1 hr. and then warmed to –50° C. for an additional ~10 hrs. After this time, the reaction was allowed to warm to room temperature overnight. Stirring was then stopped, to let the salts settle over a one hour period. The remaining yellow solution was separated by cannula filtration. Removal of solvent from the filtrate left an orange oily solid. Recrystallization from pentane at –78° C. left a pale yellow oily solid. Yield 15.0 g, 88%.

Preparation of $(C_5(CH_3)_4H$—$Si(CH_3)_2$—p—$C_6F_4B(C_6F_5)_3.Li(Et_2O)_4)$ (2): n-BuLi (1.56 mL, 2.5M in hexanes) was slowly syringed into a –78° C. $Et_2O$ (~20 mL) solution of 1 (1.6 g) and stirred for 10 min. This mixture was then quickly added via cannula to a –78° C. $Et_2O$ (~40 mL) solution of $B(C_6F_5)_3$. Immediately upon addition a yellow solution formed. The flask was stirred at –78° C. for an additional 14 hours and then left to warm to room temperature overnight. The product formed a yellow solution. Solvent was removed under vacuum and the product was washed 2× with ~20 mL pentane. After pumping dry, a white crystalline solid was isolated. Yield 3.2 g, 81%. Note: This reaction does not proceed if pentane is used instead of diethylether ($Et_2O$) as the solvent.

Preparation of $(C_5(CH_3)_4$—$Si(CH_3)_2$—p—$C_6F_4B(C_6F_5)_3.Li_2(i-Pr_2O)_4)$ (3): n-BuLi (1.15 mL, 2.5M in hexanes) was syringed into a stirred –78° C. isopropyl ether (~40 mL) solution of 2 and then warmed to room temperature on its own. Stirring was continued overnight and left a white solid suspended in solution. The isopropyl ether was removed via cannula filtration to leave a white crystalline solid which was then washed 1× with pentane (20 mL) and pumped dry. Yield 2.54 g, 77%. Note: Removal of the Cp methine proton does not proceed to completion in either $Et_2O$ or THF due to the formation of an oily layer at the bottom, possibly a calathrate. Longer reaction times (2.5 days) produces no difference in the recovered yield of 3. Use of greater than 1 equivalent of n-BuLi is also ineffective. Use of a smaller alkyl lithium such as methyl lithium (MeLi) does not work either. A mixture of unidentified products is recovered in this case. The use of lithium dimethyl amide ($LiN(CH_3)_2$) produces results similar to that when 1.1 equivalent of n-BuLi is used (i.e. ~50% conversion to 3).

Preparation of $(ZrCl_3(\eta^5—C_5(CH_3)_4—Si(CH_3)_2—p—C_6F_4B(C_6F_5)_3.Li(i-Pr_2O)_4)$ (4): 0.708 g of 3 was suspended in i-$Pr_2O$(~10 mL) and cooled to –78° C. 1.1 equiv. of $ZrCl_4$ (144 mgs) was then added slowly via side arm addition funnel. Upon addition, a yellow oil formed but the reaction was allowed to warm to room temperature and stirred overnight. The solution was concentrated and when the stirring was stopped a yellow oil layer was deposited at the bottom of the flask. The excess (iPr)$_2$O was cannulated off, then pumped dry. The product was then dissolved in ~30 mL $CH_2Cl_2$ and left to let the salts settle. The supernatant was then filtered through medium porosity filter paper. The $CH_2Cl_2$ was removed to leave a yellow crystalline solid. Successive recrystallization from $CH_2Cl_2$/pentane left a yellow oily solid which became crystalline after vacuum was applied. Yield 0.790 g, 52%. Note: Mixing 3 and $ZrCl_4$ in a 1:1 ratio together before adding cold i-$Pr_2O$ produces similar results. Likewise, vacuum transferring i-$Pr_2O$ onto 3 and $ZrCl_4$ also gives 4. In all cases, the product needs to be washed with a little i-$Pr_2O$ to remove any 2 which is formed in the reaction. Use of only 0.95 equiv. of $ZrCl_4$ in any reaction leaves traces of 3 which cannot be removed easily. If the reaction is done in $CH_2Cl_2$ some decomposition of the ligand is observed.

Preparation of $(Zr(CH_2Ph)_3(\eta^5—C_5(CH_3)_4—Si(CH_3)_2—p—C_6F_4B(C_6F_5)_3.Li(Et_2O)_4)$ (5): 0.200 g of 4 was suspended in ~10 mL of $Et_2O$ and cooled to –78°. BzMgCl (161 μL, 3.2 eq) was syringed in and the reaction was allowed to warm to room temperature. A bright yellow solution formed immediately and was left stirring for 8 hrs. Solvent was stripped and the product dissolved in $CH_2Cl_2$ to separate the salts. The solution was cannula filtered and dried under vacuum to leave a bright yellow solid. Yield not established. Note: This reaction does not proceed well in i-$Pr_2O$.

Preparation of $(ZrCl_2(\eta^5—C_5H_4)Si(CH_3)_3)(\eta^5—C_5(CH_3)_4—Si(CH_3)_2—p—C_6F_4B(C_6F_5)_3.Li(i-Pr_2O)_4)$ (6): 0.475 g of 4 was mixed with 0.045 g of LiCp—SiMe$_3$ (base free). ~10 mL of cold (–78° C.) $CH_2Cl_2$ was cannulated onto the two solids and stirred at room temperature for 2 hrs. A yellow solution formed. Stirring was stopped, the salts were allowed to settle and the solution was collected via cannula filtration. Successive $CH_2Cl_2$/pentane recrystallizations left a yellow crystalline solid. Yield is quantitative by $^1$HNMR.

Preparation of $(Zr(CH_3)_2\{\eta^5—C_5H_4)Si(CH_3)_3)(\eta^5—C_5(CH_3)_4—Si(CH_3)_2—p—C_6F_4B(C_6F_5)_3.Li(i-Pr_2O)_4(7)$: 0.175 g of (6) was suspended in ~10 mL of $Et_2O$ and cooled to –78° C. 2.5 equiv. $CH_3MrBr$ was syringed in and the reaction kept cold for 1 hr. It was then warmed to room temperature and stirred for 5 hrs. The resulting solution was filtered and then solvent was removed under vacuum to leave a yellow solid.

In situ generation of $[Zr(CH_3)(THF)(\eta^5—C_5H_4Si(CH_3)_3)(\eta^5—C_5(CH_3)_4—Si(CH_3)_2—p—C_6F_4B(C_6F_5)_3)]$; 0.33 g of (7) was dissolved in THF$_{d-8}$ and cooled to –10° C. One equivalent of trispentaflourophenyl boron was then added via spatula to the sample and warmed to room temperature immediately. A $^1$HNMR spectrum was recorded within 10 minutes and exhibited reasonances consistent with the formation of the compound. Spectroscopic data: $^1$HNMR δ0.22 (s,3H,Zr—CH$_3$); δ0.63(br s,6H,—Si(CH$_3$)$_2$—);δ0.30(2,9H, —Si(CH$_3$)$_3$); δ1.79 (s,3H,Cp—CH$_3$);δ1.88 (2,3H,Cp— CH$_3$);δ1.99 (s,3H,Cp—CH$_3$);δ1.99(s,3H,Cp—CH$_3$);δ5.72(br s,1H,TMS—Cp);δ5.95(br s,1H,TMS—Cp);δ6.40(br s,1H,TMS—Cp);δ6.50(br s,1H, TMS—Cp).

CATALYST PREPARATION

All procedures were performed under a dry nitrogen atmosphere. All liquids/solvents were anhydrous.

Catalyst A, 15 mg(0.0097 mmol) of $(Zr(Cl_2[\{\eta^5—C_5H_4)(Si(CH_3)_3)](\eta^5—C_5(CH_3)_4)—Si(CH_3)_2—p—C_6F_4B(C_6F_3)]\}.L$ were dissolved in 2.0 g of a MAO/toluene solution (13 weight percent aluminum, 9.63 mmol Al, Al/Zr= 1000) at room temperature. The catalyst was used immediately after preparation.

Catalyst B, 4 mg (0.0099 mmol) of $(\eta^5—C_5H_4n-Bu)_2 ZrCl_2$ were dissolved in 2.0 g of a MAO/toluene solution (13 weight percent aluminum, 9.63 mmol Al, Al/Zr=1000) at room temperature.

POLYMERIZATION

Ethylene/1-hexene copolymers were prepared by these catalysts under identical polymerization procedures, described below:

A 1 gallon stainless steel autoclave at room temperature was charged with 1500 mL heptane and 150 mL 1-hexene. 1.0 mL of 14 weight percent tri-iso-butylaluminum in hexane were added. The reactor was closed, and the temperature was brought to 70° C. 50 mg of catalyst B was introduced with ethylene pressure. Ethylene wasa replenished on demand to keep reactor pressure constant at 135 psi. After 60 minutes, the reactor was vented and cooled to room temperature. 42.1 gm polymer were collected.

| Catalyst Activity | A | B |
|---|---|---|
| kg/gZr/hr | 170 | 1870 |
| I$_2$ (g/10 min.) | 0.07 | 0.04 |
| MFR | 17.3 | 18.1 |
| Density (g/cc) | 0.916 | 0.917 |
| Mole % C$_6$ | 2.1 | 1.0 |
| Melting Pt. (°C.) | 111.2 | 118.5 |

What is claimed is:

1. A compound of the formula (V)(E)(W) M—L in which M is selected from the group consisting of zirconium, hafnium and titanium;

in which each of V, E, W is the same or different and each is alkyl of 1 to 6 carbon atoms, halide, or unsubstituted or substituted cyclopentadienyl provided that one, and only one, of V, E, and W, is unsubstituted or substituted cyclopentadienyl; and in which L is

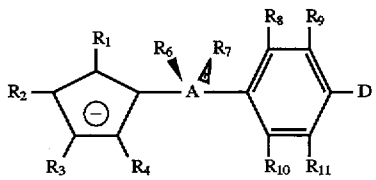

wherein each of $R_1$, $R_2$, $R_3$, $R_4$, is hydrogen, alkyl of 1 to 6 carbon atoms, alkylene of 2 to 10 carbon atoms which form bridged bicyclic or tricyclic moieties;

A is C, Si, Ge; and each of $R_6$ and $R_7$ is the same or different and is alkyl of 1 to 20 carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$, is the same or different, and is fluorine, hydrogen, alkyl of 1 to 6 carbon atoms;

D is hydrogen, alkyl of 1 to 6 carbon atoms, sodium, lithium, halogen, $BG_3$ or $AlG_3$ in which B is boron (B) and Al is aluminum (Al), and G is pentafluorophenyl, bis-trifluoromethylphenyl, phenyl or alkyl of 1 to 6 carbon atoms.

2. The compound of claim 1, wherein D is $BG_3$.

3. The compound of claim 2, wherein G is pentafluorophenyl.

4. The compound of claim 1, wherein each of $R_1$, $R_2$, $R_3$, and $R_4$, is methyl.

5. The compound of claim 1, wherein A is Si.

6. The compound of claim 5, wherein each of $R_6$ and $R_7$ is alkyl of 1 to 6 carbon atoms.

7. The compound of claim 6, wherein G is pentaflurophenyl.

8. A compound of the empirical formula (V)(E)(L)M⁺ in which M is selected from the group consisting of zirconium, hafnium and titanium;

in which each of V and E is the same or different and each is alkyl of 1 to 6 carbon atoms, halide, or unsubstituted or substituted cyclopentadienyl provided that one, and only one, of V, and E is unsubstituted or substituted cyclopentadienyl; and in which L is

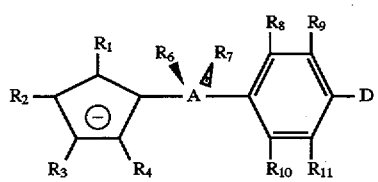

wherein each of $R_1$, $R_2$, $R_3$, $R_4$, is hydrogen, alkyl of 1 to 6 carbon atoms, alkylene of 2 to 10 carbon atoms which form bridged bicyclic or tricyclic moieties;

A is C, Si, or Ge; and each of $R_6$ and $R_7$ is the same or different and is alkyl of 1 to 20 carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$ is the same or different, and is fluorine, hydrogen, alkyl of 1 to 6 carbon atoms;

D is hydrogen, alkyl of 1 to 6 carbon atoms; sodium; lithium; halogen; alkyl halide in which the alkyl has 1 to 6 carbon atoms and halide is chlorine or bromine; or $BG_3$ or $AlG_3$ in which B is boron (B) and Al is aluminum (Al), G is selected from the group consisting of pentafluorophenyl, trifluoromethyl, phenyl, hydrogen and alkyl of 1 to 6 carbon atoms.

9. The compound of claim 8, wherein A is Si.

10. The compound of claim 9, wherein each of $R_6$ and $R_7$ is alkyl of 1 to 6 carbon atoms.

11. The compound of claim 10, wherein G is pentaflurophenyl.

12. A process for olefin polymerization comprising contacting ethylene with a transition metal catalyst, under olefin polymerization conditions, in which the source of transition metal is the compound of claim 1.

13. A process for olefin polymerization comprising contacting ethylene with a transition metal catalyst, under olefin polymerization conditions, in which the source of transition metal is the zwitterion of claim 8.

14. A process for forming the compound of claim 1 comprising contacting a compound of the formula

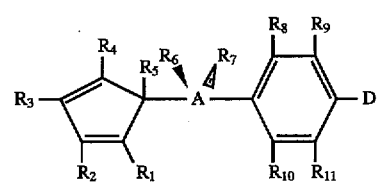

with a reagent effective to abstract the $R_5$ group to form an intermediate and contacting the intermediate with a transition metal halide, in which the transition metal is selected from the group consisting of zirconium, hafnium and titanium, to form a trihalide transition metal salt of the intermediate.

15. The process of claim 14, which further comprises the step of contacting the trihalide transition metal salt with a compound which is a lithium salt of cyclopentadienyl compound which comprises an unsubstituted or substituted cyclopentadienyl ring which is mono, di-, tri, tetra or pentasubstituted cyclopentadienyl, in which the substituion is monoalkyl, dialkyl, trialkyl, tetraalkyl or pentaalkylsubstituted cyclopentadienyl in which the alkyl is 1 to 6 carbon atoms.

16. A salt in which the anion is characterized by the formula

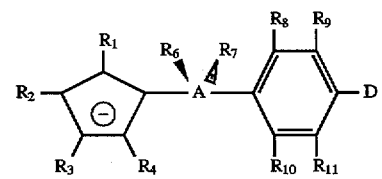

wherein each of $R_1$, $R_2$, $R_3$, $R_4$ is hydrogen, alkyl of 1 to 6 carbon atoms, alkylene of 2 to 10 carbon atoms which form bridged bicyclic or tricyclic moieties;

A is C, Si, Ge; and each of $R_6$ and $R_7$ is the same or different and is alkyl of 1 to 20 carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$, is the same or different, and is fluorine, hydrogen, alkyl of 1 to 6 carbon atoms;

D is hydrogen, alkyl of 1 to 6 carbon atoms, alkali metal; halogen; alkyl halide in which the alkyl has 1 to 6 carbon atoms and halide is chlorine or bromine; and $BG_3$ or $AlG_3$ in which B is boron (B) or Al is aluminum (Al), and G is pentafluorophenyl, bis-trifluoromethylphenyl, phenyl or alkyl of 1 to 6 carbon atoms.

17. A compound of the formula

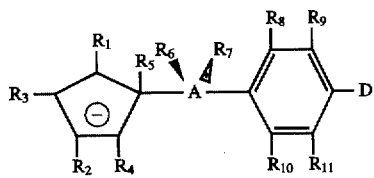

wherein each of $R_1$, $R_2$, $R_3$, $R_4$ is hydrogen, alkyl of 1 to 6 carbon atoms, alkylene of 2 to 10 carbon atoms which form bridged bicyclic or tricyclic moieties;

$R_5$ is hydrogen or $GeZ_3$ wherein Ge is germanium and Z is hydrogen or all alkyl of 1 to 6 carbon atoms;

A is C, Si, Ge; and each of $R_6$ and $R_7$ is the same or different and is alkyl of 1 to 20 carbon atoms, aryl of 6 to 20 carbon atoms, alkenyl of 2 to 20 carbon atoms or alkynyl of 3 to 20 carbon atoms;

each of $R_8$, $R_9$, $R_{10}$, $R_{11}$, is the same or different, and is fluorine, hydrogen, alkyl of 1 to 6 carbon atoms;

D is hydrogen, alkyl of 1 to 6 carbon atoms, alkali metal; halogen; alkyl halide in which the alkyl has 1 to 6 carbon atoms and halide is chlorine or bromine; and $BG_3$ or $AlG_3$ in which B is boron (B) or Al is aluminum (Al), and G is pentafluorophenyl, bis-trifluoromethylphenyl, phenyl or alkyl of 1 to 6 carbon atoms.

18. The compound of claim 17, wherein D is Br.

19. The compound of claim 17, wherein D is Li.

* * * * *

UNITED STATES PATENT AND TRADEMARK OFFICE
CERTIFICATE OF CORRECTION

PATENT NO. : 5,712,354
DATED : January 27, 1998
INVENTOR(S) : James M. Boncella, et al.

It is certified that error appears in the above-indentified patent and that said Letters Patent is hereby corrected as shown below:

Claim 16, column 10, line 63, after "alkali metal" insert --selected from the group consisting of sodium and lithium-- and in line 64 after "halogen" insert --selected from the group consisting of chloride and bromide.--

Claim 17, column 12, line 8 after "alkali metal" insert --selected from the group consisting of sodium and lithium-- and in line 9 after "halogen" insert --selected from the group consisting of chloride and bromide.--

Signed and Sealed this

Thirtieth Day of June, 1998

*Attest:*

BRUCE LEHMAN

*Attesting Officer*  Commissioner of Patents and Trademarks